United States Patent [19]
Fujisawa et al.

[11] Patent Number: 5,278,875
[45] Date of Patent: Jan. 11, 1994

[54] PROCESS FOR SYNTHESIS OF 11C-LABELED METHYL IODIDE AND APPARATUS

[75] Inventors: Yoshiki Fujisawa; Shigeki Yamazaki; Hideyuki Nakagawa; Naoko Takahashi, all of Tokyo, Japan

[73] Assignee: NKK Corporation, Tokyo, Japan

[21] Appl. No.: 913,696

[22] Filed: Jul. 16, 1992

Related U.S. Application Data

[62] Division of Ser. No. 716,868, Jun. 18, 1991, Pat. No. 5,217,675.

[30] Foreign Application Priority Data

Jun. 18, 1990 [JP] Japan ................... 2-159276
Jun. 18, 1990 [JP] Japan ................... 2-159277
Jun. 18, 1990 [JP] Japan ................... 2-159278

[51] Int. Cl.$^5$ ............................................. G21G 1/10
[52] U.S. Cl. ................................. 376/195; 73/61.77
[58] Field of Search ............... 376/190, 192-201; 250/432 PD; 73/61.77

[56] References Cited

U.S. PATENT DOCUMENTS 3,364,731 1/1968 Hook .................. 73/61.77

OTHER PUBLICATIONS

International Journal of Applied Radiation & Isotopes, vol. 36, No. 4, Apr. 1985, pp. 303-306.
Vandewalle et al., Int. J. Appl. Radiat. Isot., vol. 36, No. 6, pp. 469-474, 1985, "Fully Automatic Microprocessor-controlled System for the Production of $CO_2$, $CH_3I$, and C-Labeled Radiopharmaceuticals".

*Primary Examiner*—Daniel D. Wasil
*Attorney, Agent, or Firm*—Sughrue, Mion, Zinn, Macpeak & Seas

[57] ABSTRACT

In a process for the synthesis of $^{11}C$-labeled methyl iodide which comprises producing $^{11}CO_2$ by the irradiation of a proton beam, supplying $^{11}CO_2$ gas to a collector of $^{11}CO_2$ gas, bubbling $^{11}CO_2$ gas into a reducing agent solution to reduce $^{11}CO_2$, removing the reducing agent solution by evaporation, synthesizing $^{11}CH_3I$ from the reduced product of $^{11}CO_2$, and recovering $^{11}CH_3I$ by distillation, the termination point of the $^{11}CO_2$ gas supply, the termination point of the bubbling, the termination point of the evaporation of the reducing agent solution or the termination point of the distillation of $^{11}CH_3I$ is decided by a radiation sensor provided in the vicinity of the reaction vessel or a transfer tube connecting the target box wherein $^{11}CO_2$ gas is generated or a temperature sensor provided in an exhaust tube of the reaction vessel. The synthesizing time is shortened, and the yield of $^{11}CH_3I$ is improved by improving the utilization of $^{11}CO_2$ gas and the recovery of $^{11}CH_3I$ of which the half-life is very short.

4 Claims, 4 Drawing Sheets

PROCESS FOR SYNTHESIS OF 11C-LABELED METHYL IODIDE AND APPARATUS

This is a divisional of application Ser. No. 07/716,868 filed Jun. 18, 1991, now U.S. Pat. No. 5,217,675.

BACKGROUND OF THE INVENTION

This invention relates to process for the synthesis of a labeled compound used for the positron emission tomography (PET) system which is one imaging diagnostic technology and apparatus therefor.

A labeled compound used for the PET system is methyl iodide labeled with $^{11}C$ which was synthesized using a synthesis apparatus as shown in FIG. 7. In this figure, the numeral 1 indicates a target gas cylinder which stores a mixed gas for the target, and the target gas cylinder 1 is connected with a target box 4 in which $^{11}CO_2$ gas is produced by a transfer tube 3 through an electromagnetic valve 2. The target box 4 is connected with a collecting coil 8 by a transfer tube 7 through electromagnetic valves 5,6. A helium gas cylinder 9 is also connected with the collecting coil 8 by transfer tubes 11,7 through electromagnetic valves 10,6. The collecting coil 8 is put in a cooling vessel 12, and the outlet of the collecting coil 8 is connected with a reaction vessel 14 by a transfer tube 13. The reaction vessel 14 is further connected with a syringe 16 containing hydroiodic acid by a transfer tube 18 through an electromagnetic valve 17 as well as an exhaust tube 15.

When methyl iodide labeled with $^{11}C$ is synthesized using the above synthesis apparatus, the mixed gas for the target is filled into the target box 4 from the target gas cylinder 1 by opening the valve 2. Then, proton beam 19 supplied from a cyclotron (not shown) is irradiated for a fixed time to produce $^{11}CO_2$ gas through a nuclear reaction ($^{14}N(p,d)^{11}C$). Subsequently, the target gas containing $^{11}CO_2$ is delivered to the collecting coil 8 cooled in the cooling vessel 12 through the valves 5,6, and $^{11}CO_2$ gas is collected. After the collection is finished, the collecting coil 8 is heated to deliver $^{11}CO_2$ gas to the reaction vessel 14 by supplying helium gas from the gas cylinder 9 through the valves 10,6. In the reaction vessel 14, $^{11}CO_2$ gas is reduced by bubbling it into a reducing agent solution. Then, the reducing agent solution is evaporated by heating the reaction vessel, and discharged through the exhaust tube 15. Hydroiodic acid (HI) is introduced into the reaction vessel 14 by operating the syringe 16, and methyl iodide labeled with $^{11}C$ ($^{11}CH_3I$) is synthesized. Thereafter, $^{11}CH_3I$ is recovered by heating the reaction vessel 14 again to distill it. In the above process of synthesizing methyl iodide, respective times for terminating bubbling, the distillation of the reducing agent solution and the supply of $^{11}CO_2$ were decided from an average time necessary for these processes which was empirically decided by adding an excess time for the security. These times were inputted into an apparatus having a time control such as a microcomputer or a sequencer as a set point, and the finish of these processes was detected.

In the above conventional process, since respective termination points of the bubbling, the distillation of the reducing agent solution and the supply of $^{11}CO_2$ were decided empirically, these points were set considerably longer than the minimum time due to the variations of the bubbling time, the distillation time of the reducing agent solution and the supply time of $^{11}CO_2$ caused by a delicate difference of conditions. However, the half life of $^{11}C$ is about 20 minutes which is very short, and therefore, quenching of $^{11}CO_2$ and $^{11}CH_3I$ increased by the extension of the set points. As a result, it was difficult that both the utilization of $^{11}CO_2$ and the recovery of $^{11}CH_3I$ were kept always high. That is, it was impossible to satisfy both of decreasing the risk of failure in the synthesis and increasing the yield of $^{11}CH_3I$. Moreover, another problem is in a long time from the start of supplying $^{11}CO_2$ to the recovery of $^{11}CH_3I$.

SUMMARY OF THE INVENTION

An object of the invention is to provide processes for the synthesis of $^{11}C$-labeled methyl iodide capable of improving both the utilization of $^{11}CO_2$ and the recovery of $^{11}CH_3I$.

Another object of the invention is to provide processes for the synthesis of $^{11}C$-labeled methyl iodide capable of recovering $^{11}CH_3I$ in a short time.

Still another object of the invention is to provide apparatus therefor.

The present invention has been made in order to achieve the above objects, and is characterized by providing a radiation sensor in the vicinity of the reaction vessel and deciding the termination points of the bubbling and the evaporation of the reducing agent solution by the signal transmitted from the radiation sensor.

Thus, a process for the synthesis of $^{11}C$-labeled methyl iodide of the invention comprises a $^{11}CO_2$-producing process of producing carbon dioxide gas labeled with $^{11}C$, a bubbling process of bubbling $^{11}CO_2$ gas into a reducing agent solution in a reaction vessel, a $^{11}CH_3I$ synthesis process of synthesizing $^{11}CH_3I$ from an intermediate produced by the reduction in the bubbling process and a $^{11}CH_3I$ distillation process of distilling $^{11}CH_3I$ synthesized in the $^{11}CH_3I$ synthesis process, and deciding the termination of the bubbling in the bubbling process and the termination of the distillation in the $^{11}CH_3I$ distillation process based on the variation of the radiation emitted from the reaction vessel.

An apparatus therefor comprises a target box in which $^{11}CO_2$ gas is produced, a reaction vessel in which $^{11}CH_3I$ is synthesized from $^{11}CO_2$ gas and a radiation sensor provided in the vicinity of the reaction vessel.

Another process for the synthesis of $^{11}C$-labeled methyl iodide of the invention is characterized by detecting the temperature in the reaction vessel by a temperature sensor and deciding the termination point of the evaporation of the reducing agent solution based on the temperature variation.

Thus, the process comprises a $^{11}CO_2$-producing process of producing carbon dioxide gas labeled with $^{11}C$, a bubbling process of bubbling $^{11}CO_2$ gas into a reducing agent solution in a reaction vessel, a reducing agent solution-removing process of evaporating the reducing agent solution after the termination of the bubbling, and a $^{11}CH_3I$ synthesis process of synthesizing $^{11}CH_3I$ from an intermediate produced by the reduction in the bubbling process and deciding the termination of the evaporation in the reducing agent solution-removing process based on the variation of the temperature in an exhaust tube for discharging the vapor of the reducing agent solution connected with the reaction vessel.

An apparatus therefor comprises a target box in which $^{11}CO_2$ gas is produced, a reaction vessel in which $^{11}CH_3I$ is synthesized from $^{11}CO_2$ gas and a temperature sensor for detecting the temperature of an exhaust tube for discharging the vapor of the reducing agent solution reducing $^{11}CO_2$ gas.

The other process for the synthesis of $^{11}$C-labeled methyl iodide of the invention is characterized by providing a radiation sensor on the introducing side of $^{11}CO_2$ gas and deciding the termination point of the supply of $^{11}CO_2$ gas based on the signal transmitted from the radiation sensor.

Thus, the process comprises a $^{11}CO_2$-producing process of producing carbon dioxide gas labeled with $^{11}C$, a $^{11}CO_2$-supplying process of supplying $^{11}CO_2$ gas produced in the $^{11}CO_2$-producing process to a reaction vessel and a $^{11}CH_3I$ synthesis process of synthesizing $^{11}CH_3I$ from $^{11}CO_2$ gas, and deciding the termination of the supply of $^{11}CO_2$ gas in the $^{11}CO_2$-supplying process based on the variation of the radiation on the introducing side of $^{11}CO_2$ gas.

An apparatus therefor comprises a target box in which $^{11}CO_2$ gas is produced, a reaction vessel in which $^{11}CH_3I$ is synthesized from $^{11}CO_2$ gas, a transfer tube connecting the target box with the reaction vessel, a radiation-detecting part provided at the transfer tube, and a radiation sensor provided in the vicinity of the radiation-detecting part.

DETAILED DESCRIPTION OF THE INVENTION

In the process of the invention, the termination point of the bubbling is decided by utilizing the increase of radiation due to the introduction of $^{11}CO_2$ into the reaction vessel by bubbling, and the termination point of the distillation of $^{11}CH_3I$ is decided by utilizing the decrease of radiation due to the discharge of $^{11}CH_3I$ from the reaction vessel by the distillation. That is, when the radiation becomes a maximum, it is judged that the bubbling is terminated. When the radiation becomes a minimum, it is judged that the distillation of $^{11}CH_3I$ is terminated.

The termination point of the evaporation of the reducing agent solution is decided by detecting the temperature in an exhaust tube for discharging the vapor of the reducing agent solution connected with the reaction vessel. In this process, the temperature variation due to the evaporation of the reducing agent solution is utilized, i.e., the temperature rises together with the start of the evaporation and drops by the termination of the evaporation. When the temperature in the exhaust tube becomes a minimum, it is judged that the evaporation of the reducing agent solution is terminated. The temperature variation accompanied by the evaporation of the reducing agent solution is preferably detected by measuring the temperature in the reaction vessel. However, since the corrosive action of hydroidic acid placed in the reaction vessel is very strong, it is difficult to place a temperature sensor in the reaction vessel. Therefore, the temperature sensor is attached to the exhaust tube, and the temperature in the exhaust tube is detected.

The termination point of the supply of $^{11}CO_2$ gas into the reaction vessel is decided by detecting the radiation on the introducing side of $^{11}CO_2$ gas. In this process, the fact is utilized that the radiation is great during supplying $^{11}CO_2$ gas, but it is small when the supply is terminated. When the radiation is sharply decreased, it is judged that the supply of $^{11}CO_2$ gas is terminated. The detecting point of the radiation may be any point between the target box and the reaction vessel.

The above maximum point and the minimum point of the radiation emitted from the reaction vessel, the minimum point of the temperature in teh exhaust tube, and the sharp decrease of the radiation on the introducing side of $^{11}CO_2$ gas can be decided by visual observation of various displays indicating the output of the radiation sensor. Alternatively, the output of the radiation sensor is automatically decided by inputting it into a controller such as a microcomputer, and the next work is automatically started.

EXAMPLES

Example 1

Figure 1:
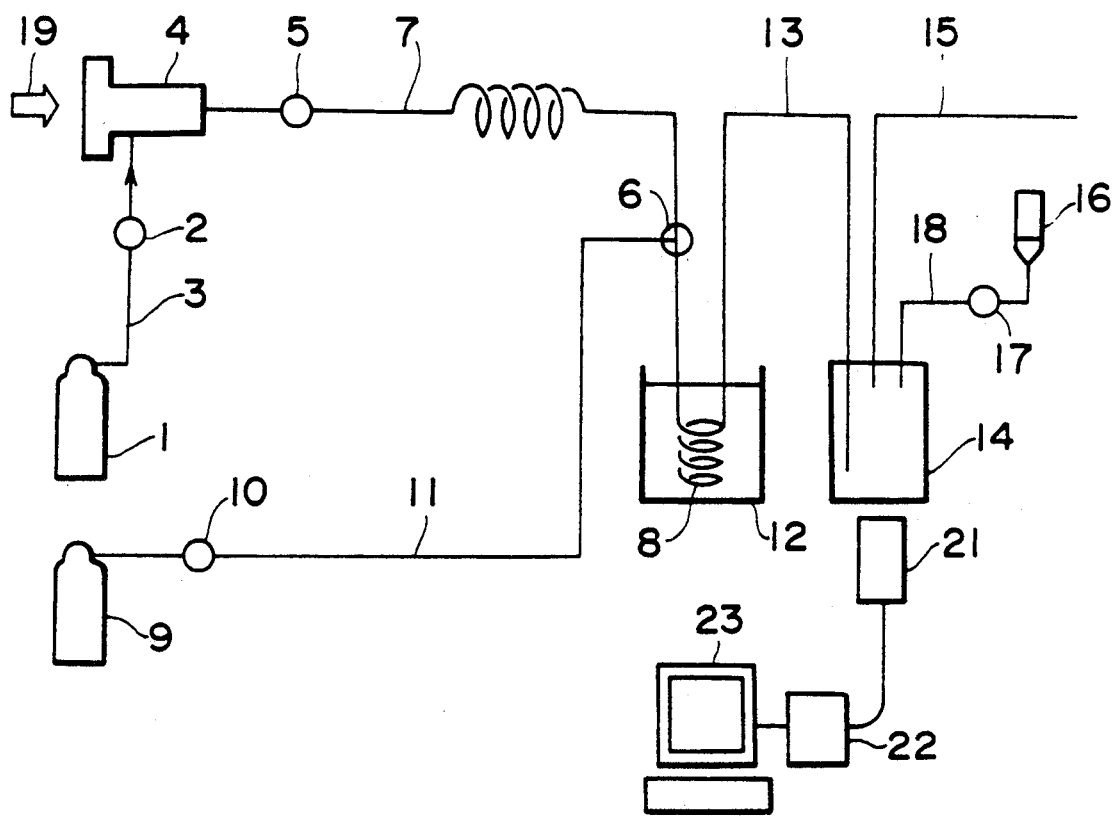
FIG. 1 is a block diagram illustrating an apparatus embodying the invention.

An apparatus for the synthesis of $^{11}$C-labeled methyl iodide is shown in FIG. 1. The apparatus is composed of a target gas cylinder 1 which stores a mixed gas for the target, and the target gas cylinder 1 is connected with a target box 4 in which $^{11}CO_2$ gas is produced by a transfer tube 3 through an electromagnetic valve 2. The target box 4 is connected with a collecting coil 8 by a transfer tube 7 through electromagnetic valves 5, 6. A helium gas cylinder 9 is also connected with the collecting coil 8 by transfer tubes 11, 7 through electromagnetic valves 10, 6. The collecting coil 8 is put in a cooling vessel 12, and the outlet of the collecting coil 8 is connected with a reaction vessel 14 by a transfer tube 13. The reaction vessel 14 is further connected with a syringe 16 containing hydroiodic acid by a transfer tube 18 through an electromagnetic valve 17 as well as an exhaust tube 15. A radiation sensor 21 is disposed adjacent to the reaction vessel, and the radiation sensor 21 is connected with a personal computer 23 through an A/D converter 22.

Figure 2:
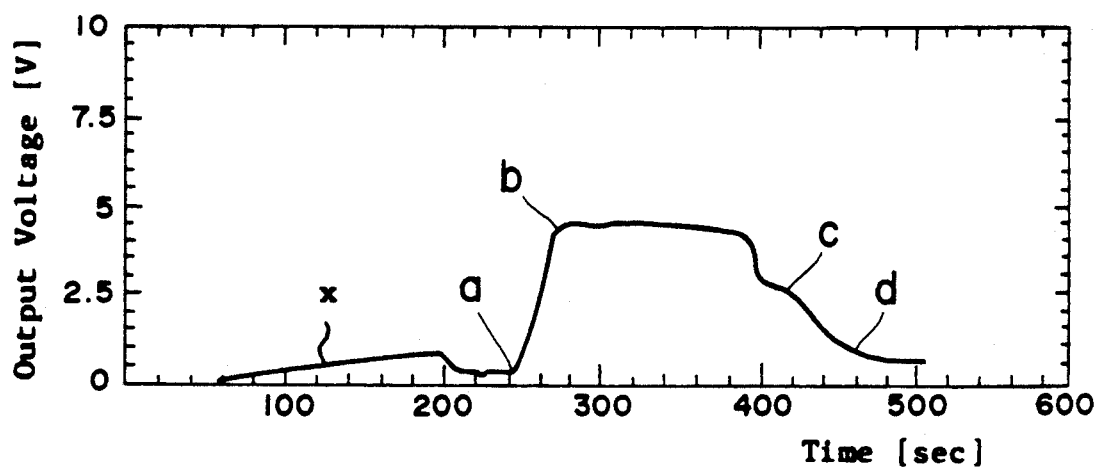
FIG. 2 is a chart indicating an output curve of a radiation sensor obtained by using the apparatus of FIG. 1.

$^{11}$C-labeled methyl iodide was produced using the above apparatus. As the mixed gas for the target, highly pure $N_2$ gas (99.999%) or a mixed gas of 90% of $N_2$ gas and 10% of $O_2$ gas was used, and filled into the target box 4 from the target gas cylinder 1 by opening the valve 2 at a pressure of 5-30 kg/cm$^2$. Then, proton beam 19 supplied from a cyclotron (not shown) was irradiated for 10-60 minutes to produce $^{11}CO_2$ gas through a nuclear reaction ($^{14}$N(p.d)$^{11}$C). Subsequently, the target gas containing $^{11}CO_2$ was delivered to the collecting coil 8 cooled at −186° C. by the cooling vessel 12 through the valves 5,6, and $^{11}CO_2$ gas was collected. After the collection was finished, the collecting coil 8 was heated to deliver $^{11}CO_2$ gas to the reaction vessel 14 by supplying helium gas from the gas cylinder 9 through the valves 10,6. In the reaction vessel, $^{11}CO_2$ gas was reduced by bubbling it into 50-30 μl of (a saturated solution of LiAlH$_4$ and THF) solution as the reducing agent solution. The radiation emitted from the reaction vessel 14 was measured by the radiation sensor 21, and the electric signal outputted therefrom was converted to a digital signal by the A/D converter 22. The digital signal was inputted in the microcomputer 23. The microcomputer 23 treated the digital signal data to indicate the strength of the radiation on a display as a voltage value, and decided the termination point of the bubbling. The output voltage curve x was as shown in FIG. 2. When the bubbling was started, the output voltage rose from the starting point a of the bubbling. The output voltage rise was stopped at the termination point b of the bubbling. The termination point b was decided by the microcomputer 23, and the computer 23 instructed to start heating of the reaction vessel 14. The reducing agent solution was evaporated by the heating, and discharged through the exhaust tube 15. Thus, a complex of $^{11}CO_2$ and $LiAlH_4$ remained in the reaction vessel 14 as the intermediate. 1 ml of 55–58% hydroiodic acid solution was introduced into the reaction vessel 14 by operating the syringe 16 to synthesize methyl iodide labeled with $^{11}C$. The output voltage was almost constant from the termination of the bubbling to the $^{11}CH_3I$ synthesis. Then, the reaction vessel 14 was heated again, and $^{11}CH_3I$ was recovered by distillation. The output voltage dropped from the starting point c of the distillation, and the output voltage drop was stopped at the termination point d of the distillation. The microcomputer 23 decided the termination point of the distillation, and instructed to stop the recovery.

The synthesis time of $^{11}CH_3I$ was 7–8 minutes. The utilization of $^{11}CO_2$ gas was 98%, and the recovery of $^{11}CH_3I$ was 70%, whereas in the conventional process conducted using the above apparatus except the radiation sensor 21, the synthesis time was 15–20 minutes. The utilization of $^{11}CO_2$ gas was 88%, and the recovery of $^{11}CH_3I$ was 50%.

Example 2

Figure 3:
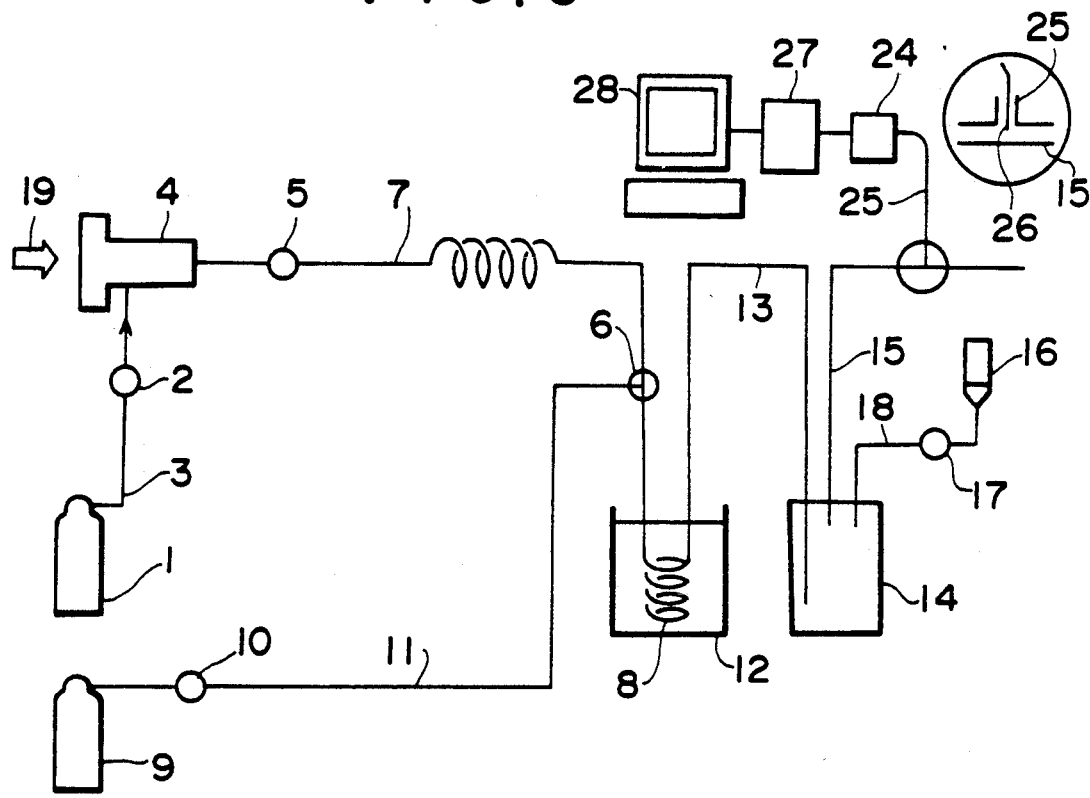
FIG. 3 is a block diagram illustrating another apparatus embodying the invention.

An apparatus for the synthesis of $^{11}C$-labeled methyl iodide is shown in FIG. 3. This apparatus is the same as employed in Example 1 except that the radiation sensor 21 is not provided but a temperature sensor 24 is provided. In detail, a branch tube 25 is connected with the exhaust tube 15, and a temperature detecting element 26 is inserted into the exhaust tube 15. The temperature detecting element 26 is connected with a microcomputer 28 through an A/D converter 27.

Figure 4:
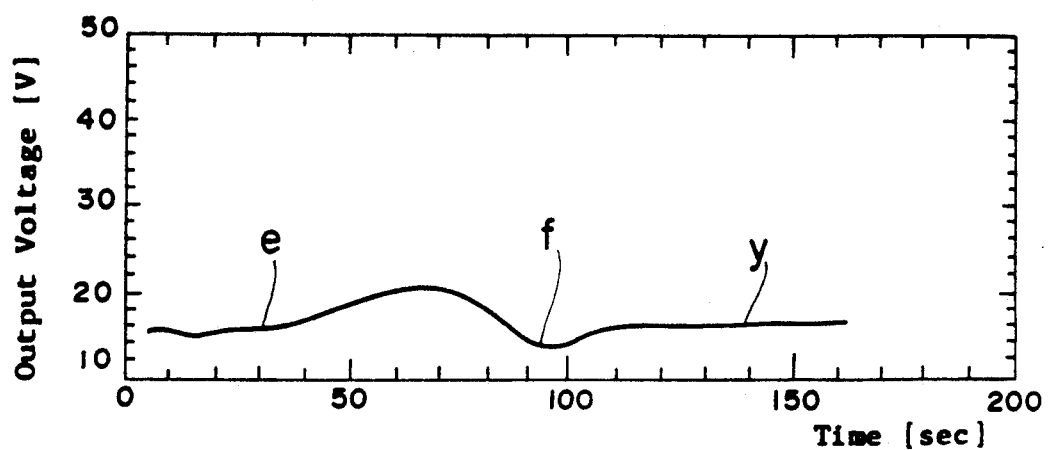
FIG. 4 is a chart indicating an output curve of a temperature sensor obtained by using the apparatus of FIG. 3.

$^{11}C$-labeled methyl iodide was produced using the above apparatus sumilar to Example 1. The bubbling time was set at the same 4–5 minutes as the conventional process, and the distillation time was set at the same 4–5 minutes as the conventional process. The temperature in the exhaust tube 15 was measured by the temperature sensor 24, and the electric signal outputted therefrom was converted to a digital signal by the A/D converter 27. The digital signal was inputted in the microcomputer 28. The microcomputer 28 treated the digital signal data to indicate the temperature on a display as a voltage value, and decided the termination point of the evaporation of the reducing agent solution. The output voltage curve y was shown in FIG. 4. After the termination of the bubbling, when the evaporation of the reducing agent solution was started, the output voltage gradually rose from the starting point 4 of the evaporation. Then, the output voltage gradually dropped, and it was a minimum at the termination point f of the evaporation. The termination point f was decided by the microcomputer 28, and the computer 28 instructed to work the syringe 16. The hydroiodic acid was injected into the reaction vessel 14, and $^{11}CH_3I$ was synthesized.

The synthesis time of $^{11}CH_3I$ was 7–8 minutes. The utilization of $^{11}CO_2$ gas was 98%, and the recovery of $^{11}CH_3I$ was 70%, whereas, in the conventional process conducted using the above apparatus except the radiation sensor 21, the synthesis time was 15–20 minutes. The utilization of $^{11}CO_2$ gas was 98%, and the recovery of $^{11}CH_3I$ was 50%.

Example 3

Figure 5:
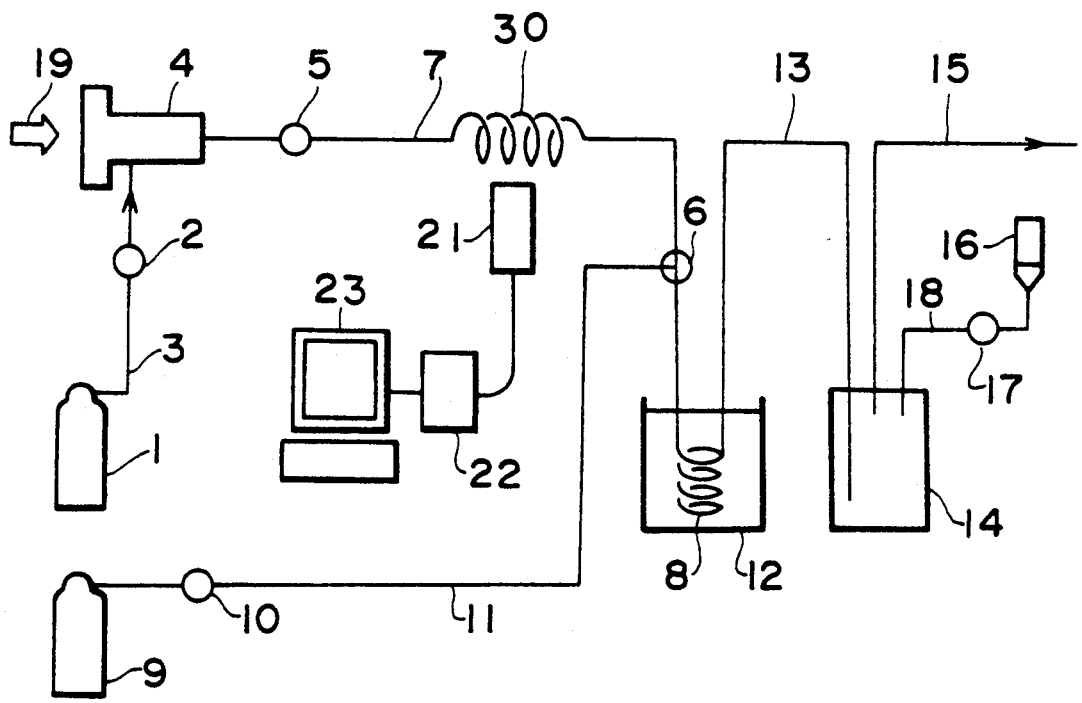
FIG. 5 is a block diagram illustrating another apparatus embodying the invention.

An apparatus for the synthesis of $^{11}C$-labeled methyl iodide is shown in FIG. 5. This apparatus is the same as Example 1 except that the radiation sensor 21 is provided near the detecting coil 30 of the transfer tube 7 connecting the target box 4 with the collecting coil 8 instead of the reaction vessel 14.

Figure 6:
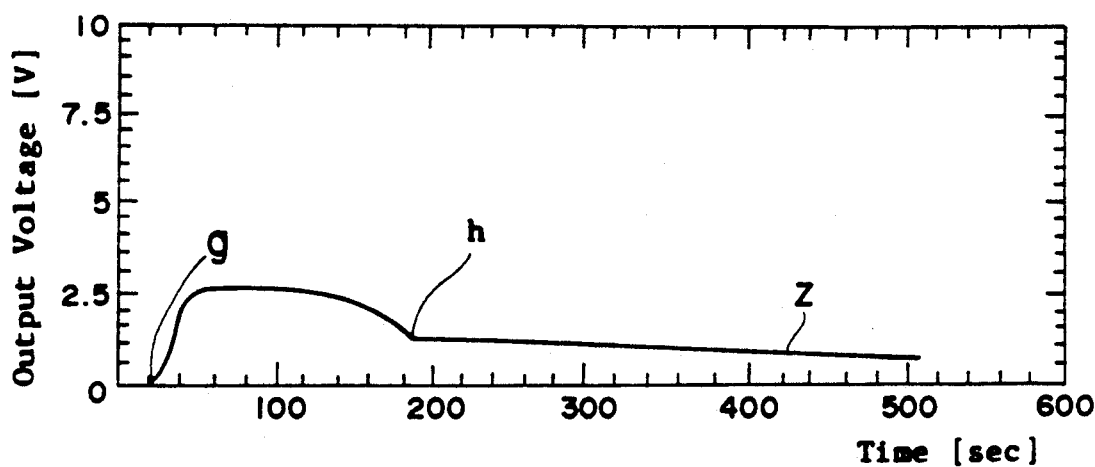
FIG. 6 is a chart indicating an output curve of a radiation sensor obtained by using the apparatus of FIG. 5.
Figure 7:
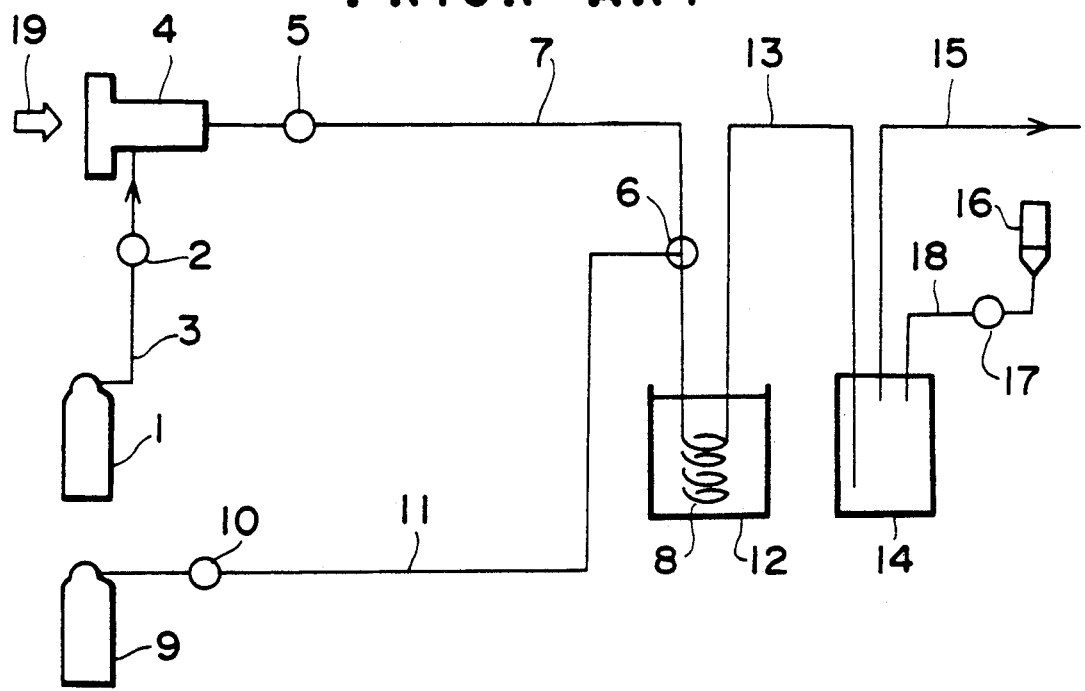
FIG. 7 is a block diagram of a conventional apparatus.

$^{11}C$-labeled methyl iodide was produced using the above apparatus similar to Example 1. The bubbling time was set at the same 4–5 minutes as the conventional process, and the distillation time was set at the same 4–5 minutes as the conventional process. The evaporation time of the reducing agent solution was set at the same 2–3 minutes as the conventional process. The output voltage curve z was shown in FIG. 6. When the supply of $^{11}CO_2$ gas was started, the output voltage rose from the starting point g of the supply. While the supply of $^{11}CO_2$ gas was almost constant, the output voltage curve z was almost constant. When the supply of $^{11}CO_2$ gas was terminated, the output voltage dropped. The computer 23 decided the termination point of the supply, and instructed to start the collection of $^{11}CO_2$ gas by the collecting coil 8.

The synthesis time of $^{11}CH_3I$ was 7–8 minutes. The utilization of $^{11}CO_2$ gas was 98%, and the recovery of $^{11}CH_3I$ was 70%, whereas in the conventional process conducted using the above apparatus except the radiation sensor 21, the synthesis time was 15–20 minutes. The utilization of $^{11}CO_2$ gas was 98%, and the recovery of $^{11}CH_3I$ was 50%.

We claim:
1. A process for the synthesis of $^{11}C$-labeled methyl iodide which comprises a $^{11}CO_2$-producing process of producing carbon dioxide gas labeled with $^{11}C$, supplying $^{11}CO_2$ gas to a reaction vessel and bubbling the $^{11}CO_2$ gas into a reducing agent solution in the reaction vessel to reduce the $^{11}CO_2$ gas to yield an intermediate, a reducing agent solution-removing process of evaporating the reducing agent solution after the termination of the bubbling, and a $^{11}CH_3I$ synthesis process of synthesizing $^{11}CH_3I$ from the intermediate produced by the reduction in the bubbling process and terminating the evaporation in the reducing agent solution-removing process based on a variation of the temperature in an exhaust tube for discharging the vapor of the reducing agent solution connected with the reaction vessel.

2. The process of claim 1, wherein said bubbling process of bubbling the $^{11}CO_2$ gas into the reducing agent solution in the reaction vessel is terminated by terminating the supply of the $^{11}CO_2$ gas based on a variation in radiation produced upon supplying the $^{11}CO_2$ gas into the reaction vessel.

3. An apparatus for the synthesis of $^{11}C$-labeled methyl iodide which comprises a target box in which $^{11}CO_2$ gas is produced, a reaction vessel in which $^{11}CH_3I$ is synthesized from said $^{11}CO_2$ gas and a temperature sensor for detecting the temperature of an exhaust tube and deciding a termination point for discharging the vapor of a reducing agent solution which has reduced $^{11}CO_2$ gas.

4. The apparatus of claim 3, which further comprises a transfer tube connecting said target box and said reaction vessel with radiation detecting means for deciding a termination point for bubbling of $^{11}CO_2$ gas provided adjacent the transfer tube.

* * * * *